(12) United States Patent
Kakade et al.

(10) Patent No.: US 7,980,491 B2
(45) Date of Patent: Jul. 19, 2011

(54) NOZZLE-BASED ATOMIZATION SYSTEM

(75) Inventors: Prashant P. Kakade, Sunnyville, CA (US); Robert C. Williams, III, Raleigh, NC (US); Perry Genova, Chapel Hill, NC (US)

(73) Assignee: Abbott Laboratories, Abbott Park, IL (US)

( * ) Notice: Subject to any disclaimer, the term of this patent is extended or adjusted under 35 U.S.C. 154(b) by 357 days.

(21) Appl. No.: 12/036,730

(22) Filed: Feb. 25, 2008

(65) Prior Publication Data

US 2008/0203193 A1      Aug. 28, 2008

Related U.S. Application Data

(60) Provisional application No. 60/903,970, filed on Feb. 28, 2007.

(51) Int. Cl.
*B05B 1/34* (2006.01)
*B05B 7/24* (2006.01)
*A61M 11/00* (2006.01)

(52) U.S. Cl. ... 239/468; 239/337; 239/463; 128/200.14; 128/200.23

(58) Field of Classification Search ............ 239/302, 239/337, 338, 461, 463, 468, 471, 490, 597–599, 239/601; 128/200.14, 200.23
See application file for complete search history.

(56) References Cited

U.S. PATENT DOCUMENTS

| | | | |
|---|---|---|---|
| 3,001,524 A * | 9/1961 | Maison et al. | 128/200.23 |
| 3,053,462 A | 9/1962 | Schloz | |
| 3,346,195 A * | 10/1967 | Groth | 239/337 |
| 3,437,270 A * | 4/1969 | Venus, Jr. | 239/118 |
| 4,074,861 A * | 2/1978 | Magers et al. | 239/492 |
| 4,972,830 A | 11/1990 | Wong et al. | |
| 5,662,271 A | 9/1997 | Weston | |
| 5,676,311 A * | 10/1997 | Hartman | 239/120 |
| 5,682,875 A * | 11/1997 | Blower et al. | 128/200.23 |
| 6,418,925 B1 | 7/2002 | Genova et al. | |
| 6,527,151 B1 | 3/2003 | Pavkov et al. | |
| 6,615,826 B1 | 9/2003 | Gabrio et al. | |
| 2008/0296318 A1 * | 12/2008 | Chevalier | 222/251 |

FOREIGN PATENT DOCUMENTS

| | | |
|---|---|---|
| DE | 933235 | 9/1955 |
| DE | 102004001222 | 3/2006 |
| WO | 0071192 | 11/2000 |

OTHER PUBLICATIONS

International Search Report for PCT/US2008/054924, mailed Feb. 11, 2009.
Newman, S., "Principles of Metered-Dose Inhalers", Respiratory Care, vol. 50, No. 9, pp. 1177-1190 (2005).

* cited by examiner

*Primary Examiner* — Darren W Gorman
(74) *Attorney, Agent, or Firm* — Portia Chen

(57) ABSTRACT

An improved atomization system for aerosolizing liquids including a vortexing nozzle and a flat or protruding face on the nozzle exit orifice. The system can also include a diverging mouthpiece insert. The present invention can produce a high fine particle fraction and modest throat deposition in conjunction with reduced aerosol plume velocity and impact force.

10 Claims, 12 Drawing Sheets

NOZZLE-BASED ATOMIZATION SYSTEM

CROSS-REFERENCE SECTION TO RELATED APPLICATIONS

This application claims priority to U.S. Application Ser. No. 60/903,970, filed Feb. 28, 2007, and is incorporated herein by reference in its entirety.

FIELD OF THE INVENTION

The invention relates to an atomization system for pressurized spray for use in various applications, including pharmaceutical applications involving pressurized metered dose inhalers, which reduces aerosol plume velocity and increases efficiency of spray delivery.

BACKGROUND OF THE INVENTION

Pressurized metered dose inhalers ("pMDIs") are common in the industry, as are conventional MDI actuators that are based on "two-orifice-and-sump" designs. Unfortunately, their commonality is accompanied by their common disadvantages: high spray velocity and inadequate particle size distribution control, which results in poor drug delivery to the patient. It is postulated that high spray velocity is one of the lead causes of high oropharyngeal drug deposition (Newman S., (2005) "Principles of Metered-Dose Inhalers", Respiratory Care, Vol. 50. No. 9. pp. 1177-1190). Previous attempts at solving this problem are evidenced by the use of spacers to reduce spray velocity (e.g. U.S. Pat. No. 4,972,830). However, spacers are bulky, and drug deposition within the spacers leads to a decrease of actual drug delivered to the patient. Other methods for slowing plume force include introducing complicated baffles or bluff bodies into the device nozzle or mouthpiece, or introducing a flow control/mixing chamber into the mouthpiece (e.g. U.S. Pat. Nos. 6,615,826 and 6,527,151). These methods, however, also have the propensity to increase drug deposition in the mouthpiece at the site of the baffles, bluff bodies, or other airflow obstructions.

Modifying the aerosol generation mechanism itself using a vortexing chamber produces a low plume force spray, as described in U.S. Pat. No. 6,418,925, which is incorporated herein by reference. According to the present invention, modifying the actuator design by using a flat or protruding nozzle face, as opposed to a "standard" concave-conical nozzle face (common in the industry) and a diverging mouthpiece insert further reduces drug deposition on the nozzle face, the device mouthpiece, and the throat of the patient.

Applicants have discovered that a flat or protruding nozzle face affects the dynamics of the aerosol flow at the nozzle orifice, which in turn affects the particle size distribution in the aerosol spray leaving the orifice. Upon actuation using the present invention, the drug-propellant mixture from the canister enters the vortex chamber of the nozzle of the present invention at an angle. The mixture flows along the periphery of the chamber which sets up a swirling motion, until the mixture leaves the device via an axial exit orifice at a decelerated velocity. The nozzle face geometry discovered by the applicants restricts the extent as well as spread of unvaporized drug-propellant mixture around the nozzle orifice, thus limiting drug deposition around on the nozzle face. The mouthpiece insert works to further decelerate the spray.

SUMMARY OF THE INVENTION

The atomization system of the present invention incorporates a vortexing nozzle with a flat or protruding exit orifice face and a diverging mouthpiece insert, which results in high fine particle fraction and modest throat deposition in conjunction with reduced aerosol plume velocity and impact force. Various embodiments of the present invention and related methods are also disclosed in the following description. The various embodiments can be used alone or in any combination, as is desired.

DETAILED DESCRIPTION

The present invention will now be described with regard to the Figures.

Figure 1:
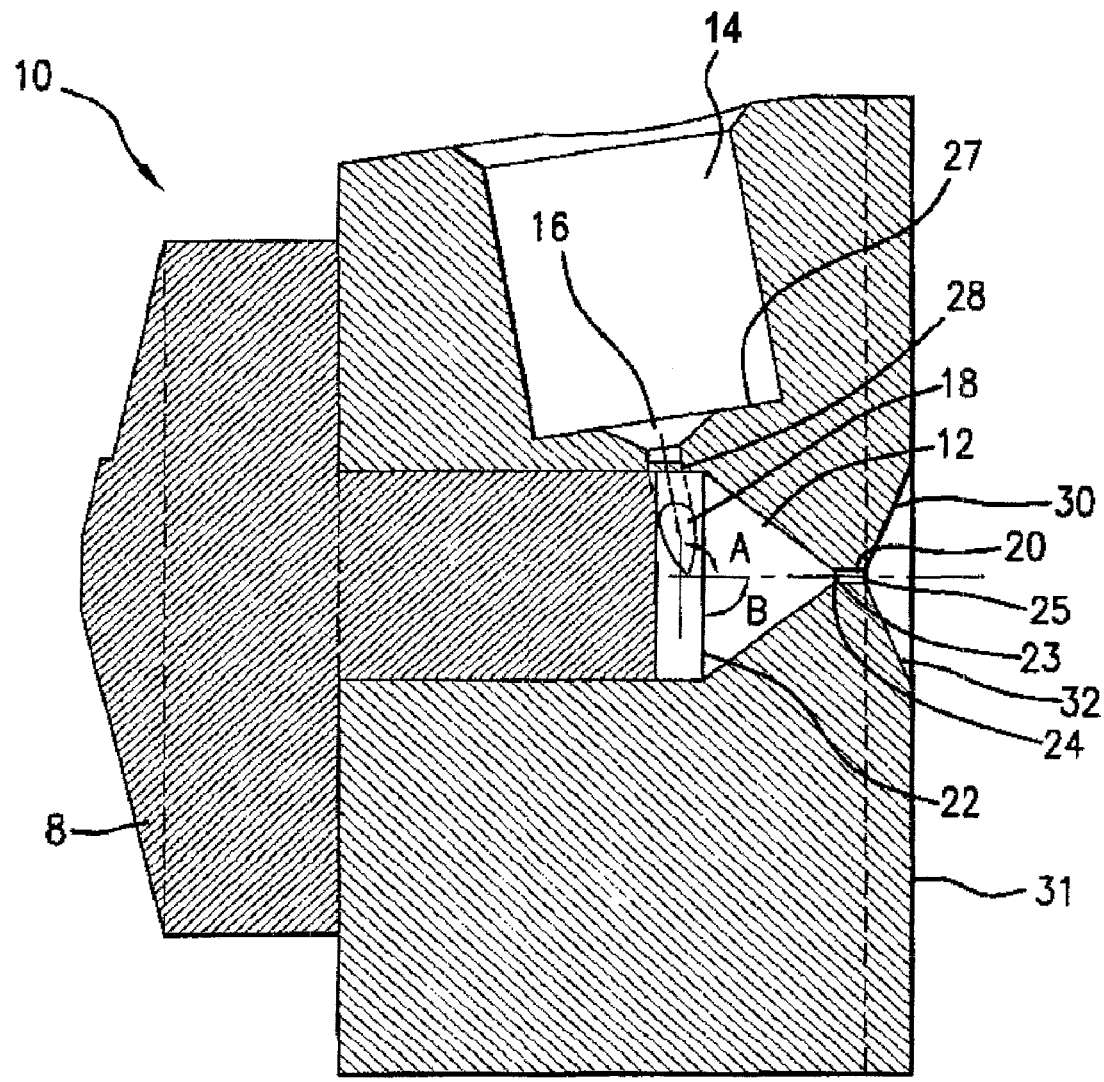
FIG. 1 is a cross section of a standard nozzle face.

FIG. 1 illustrates a cross section of an atomization system [described in U.S. Pat. No. 6,418,925]. The components of the atomization system of FIG. 1 will be consistent throughout the other Figures as follows: Nozzle 10 receives pressurized liquid through nozzle inlet 14, which has a reducing chamber 16. Reducing chamber 16 includes of a reducing chamber inlet 26, a reducing chamber outlet 28, and a reducing chamber exit 18 that is attached tangentially to swirl chamber 12 and is the point at which the pressurized liquid exits the inlet 14 and enters the swirl chamber 12. The axis of the reducing chamber outlet 28 is set at an angle A to the axis of the swirl chamber 12. Angle A is greater than 90 degrees, preferably 105 degrees.

The swirl chamber is preferably conical, where the first swirl chamber end 22 is greater than the second swirl chamber end 24. The swirl chamber cone angle B is 60 to 120 degrees, preferably 90 degrees. The second swirl chamber end 24 is connected to nozzle exit orifice 20, which is connected to nozzle face 30. Nozzle exit orifice 20 has a length 21.

As shown in FIG. 1, the nozzle face 30 includes an outer nozzle face 31, which surrounds an inner nozzle face ring 32, which is a concentric ring that immediately surrounds the exit orifice 20 on the exterior surface, or "patient side" of the nozzle, as opposed to the "canister side" of the nozzle such that the inner circumference of inner nozzle face ring 32 is equal to the circumference of the exit orifice 20. The inner nozzle face ring 32 shown in FIG. 1 is the standard and well-known "concave-conical" geometrical configuration with respect to the outer nozzle face wall 31. The diameter of the "ring" can vary depending on the nozzle used, but the configuration of the nozzle face as "concave-conical" is standard for nozzles used on aerosol dispensers.

A nozzle back seal 8 is used to close the back of the nozzle after the nozzle has been manufactured. Back seal 8 is preferably attached to the nozzle using ultrasonic welding or some other method such as by interference fit that would be known to one of skill in the art. It should also be understood that the atomization system of the present invention could also be manufactured in one piece, eliminating the need for nozzle back seal 8, using standard manufacturing methods known in the art.

Figure 2:
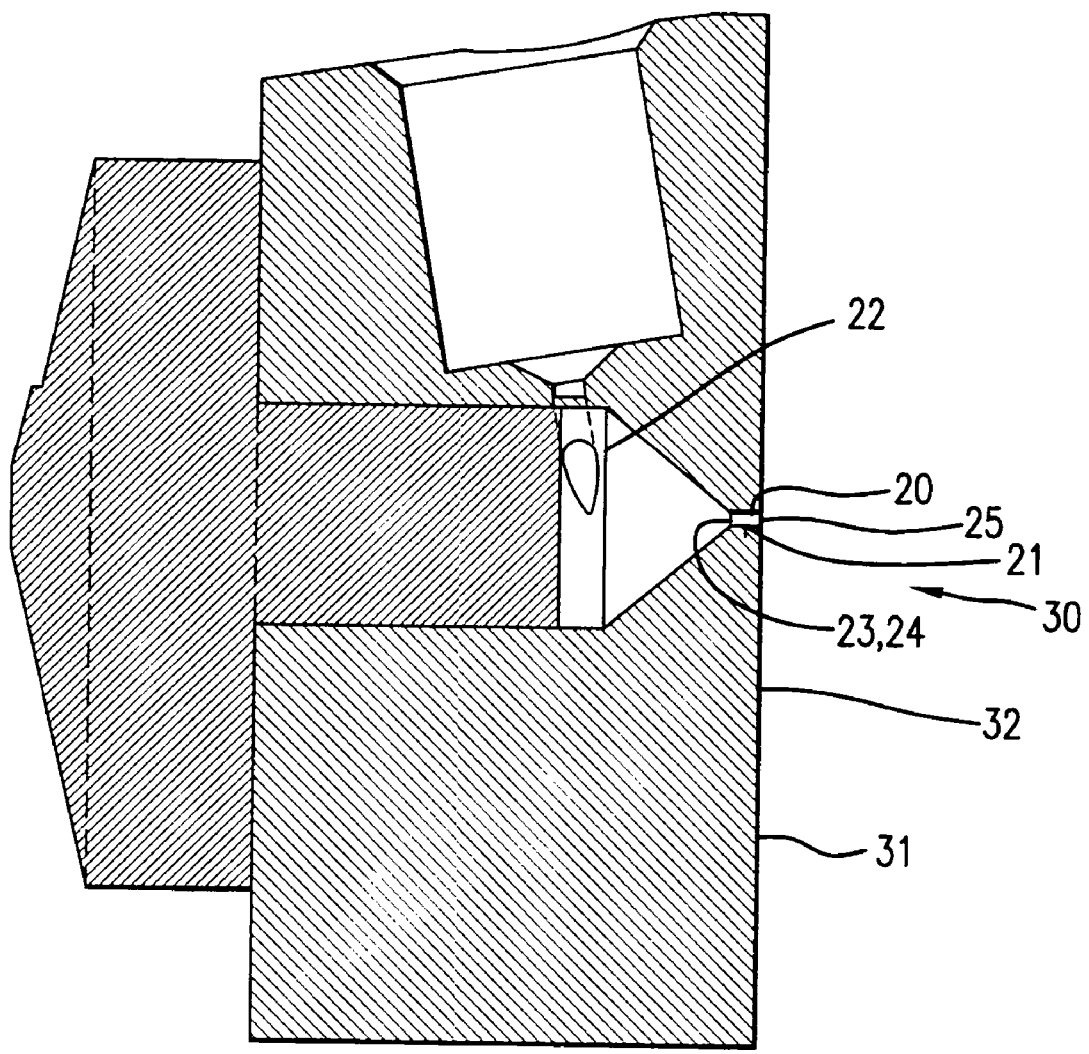
FIG. 2 is a cross section of an embodiment of the nozzle face of the present invention.

FIG. 2 illustrates the atomization system of the present invention with a flat configuration of the inner nozzle face 32. FIGS. 3 through 6 illustrate the atomization system of the present invention using different novel geometrical configurations for the inner nozzle face 32 that protrude and form a ring around nozzle exit orifice 20. The protruding ring has an inner circumference 33 and an outer circumference 34. The inner circumference 33 is flush with and directly aligns with the exit orifice 20, and preferably is equal to the circumference of exit orifice 20, so that there is a smooth surface over which the aerosolized spray travels through the exit orifice and out of the nozzle, with no obstructions that could be caused by a differential in size once the aerosolized spray leaves the exit orifice and passes through the inner nozzle face 32 ring. For all configurations shown in FIG. 3 through 6, the ring is defined by several dimensions: a height Y, which is preferably equal to or less than the length 21 of exit orifice 20, and a diameter X, which can be greater than, but is preferably equal to or less than the diameter of the first swirl chamber end 22. The exit orifice has a first exit orifice end 23 and a second exit orifice end 25 (between which spans length 21), the first exit orifice end 23 which is connected to the second swirl chamber end 24, and the second exit orifice end 25 which is distal to the swirl chamber 12. The height Y is measured from the plane of the first exit orifice end 23 to the plane of the second exit orifice end 25. As illustrated on FIG. 3, height Y is a positive number measured between the two planes.

Figure 3:
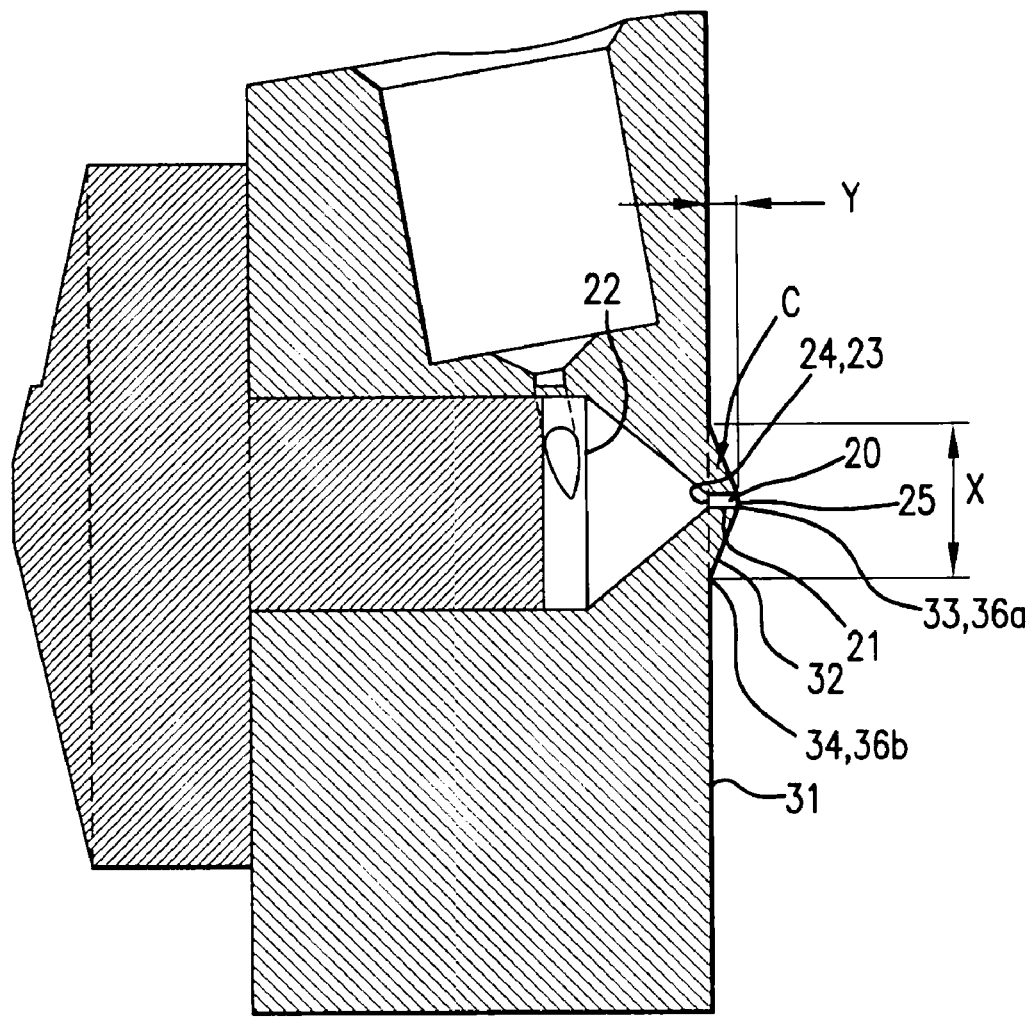
FIG. 3 is a cross section of an embodiment of the nozzle face of the present invention.

More specifically, FIG. 3 illustrates a "convex-conical" configuration for the protruding ring that forms inner nozzle face 32. This configuration can also be defined by angle C between the outer nozzle face 31 plane and the plane connecting points 36a and 36b, which is preferably 45 degrees or less.

Figure 4:
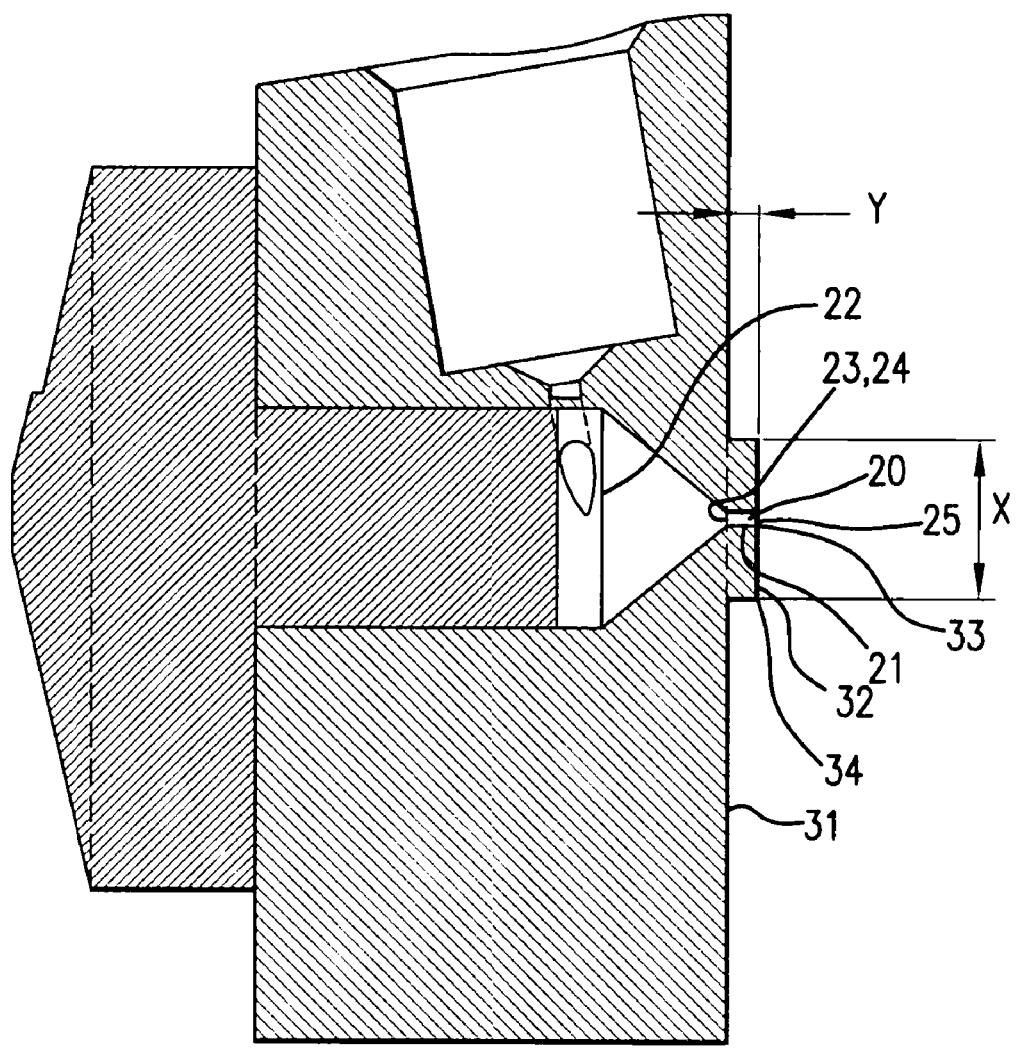
FIG. 4 is a cross section of an embodiment of the nozzle face of the present invention.
Figure 5:
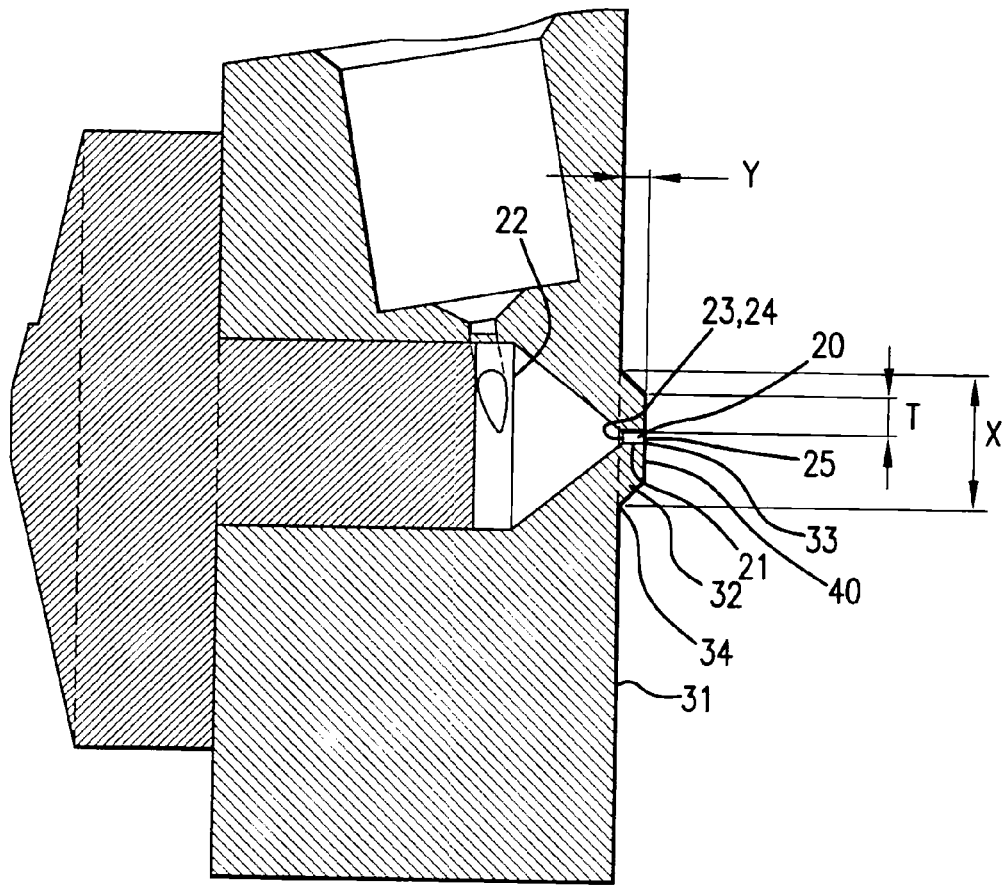
FIG. 5 is a cross section of an embodiment of the nozzle face of the present invention.
Figure 6:
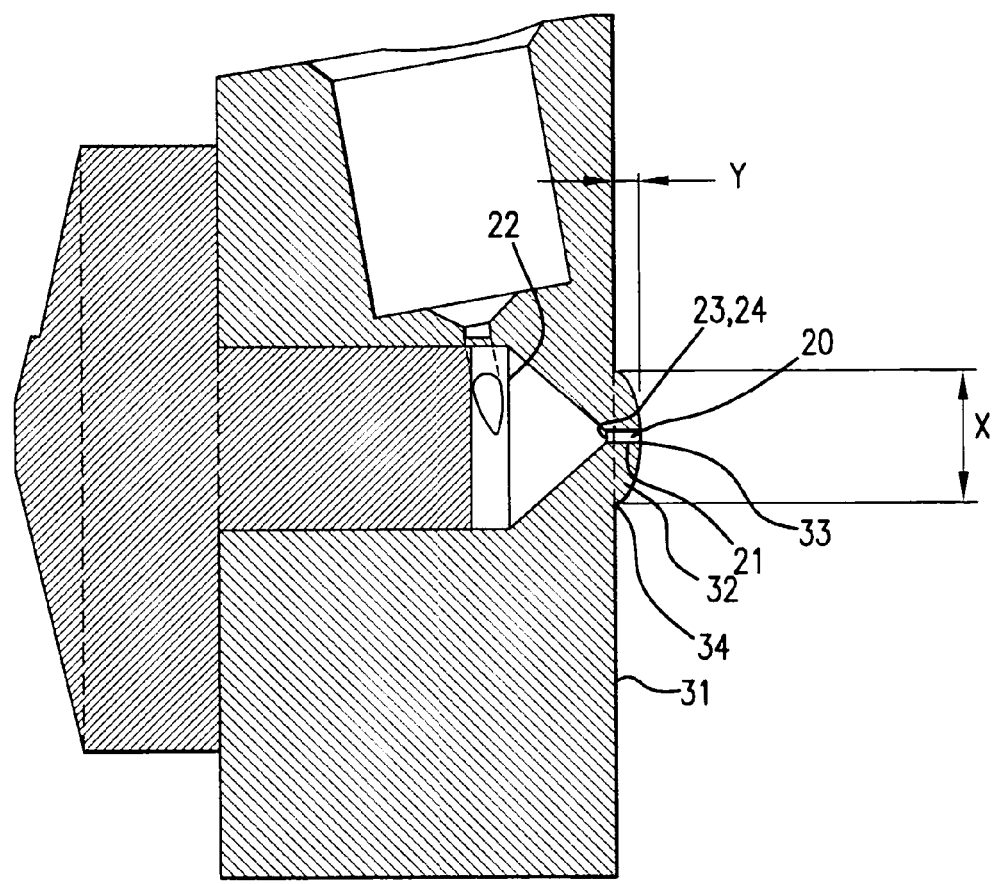
FIG. 6 is a cross section of an embodiment of the nozzle face of the present invention.

FIG. 4 illustrates a "rectangular-conical" configuration for the protruding ring that forms inner nozzle face 32. FIG. 5 illustrates a "trapezoidal-conical" configuration for the protruding ring that forms inner nozzle face 32. This configuration is also defined by a width T of the top face 40 of the trapezoidal protrusion. The top face of the trapezoid is preferably parallel to, and collinear with, the plane of the exit orifice 20. FIG. 6 illustrates a "convex-domed" configuration for the protruding ring that forms inner nozzle face 32. This configuration can also be defined by a radius of curvature R preferably equal to the length of swirl chamber 12.

Figure 7:
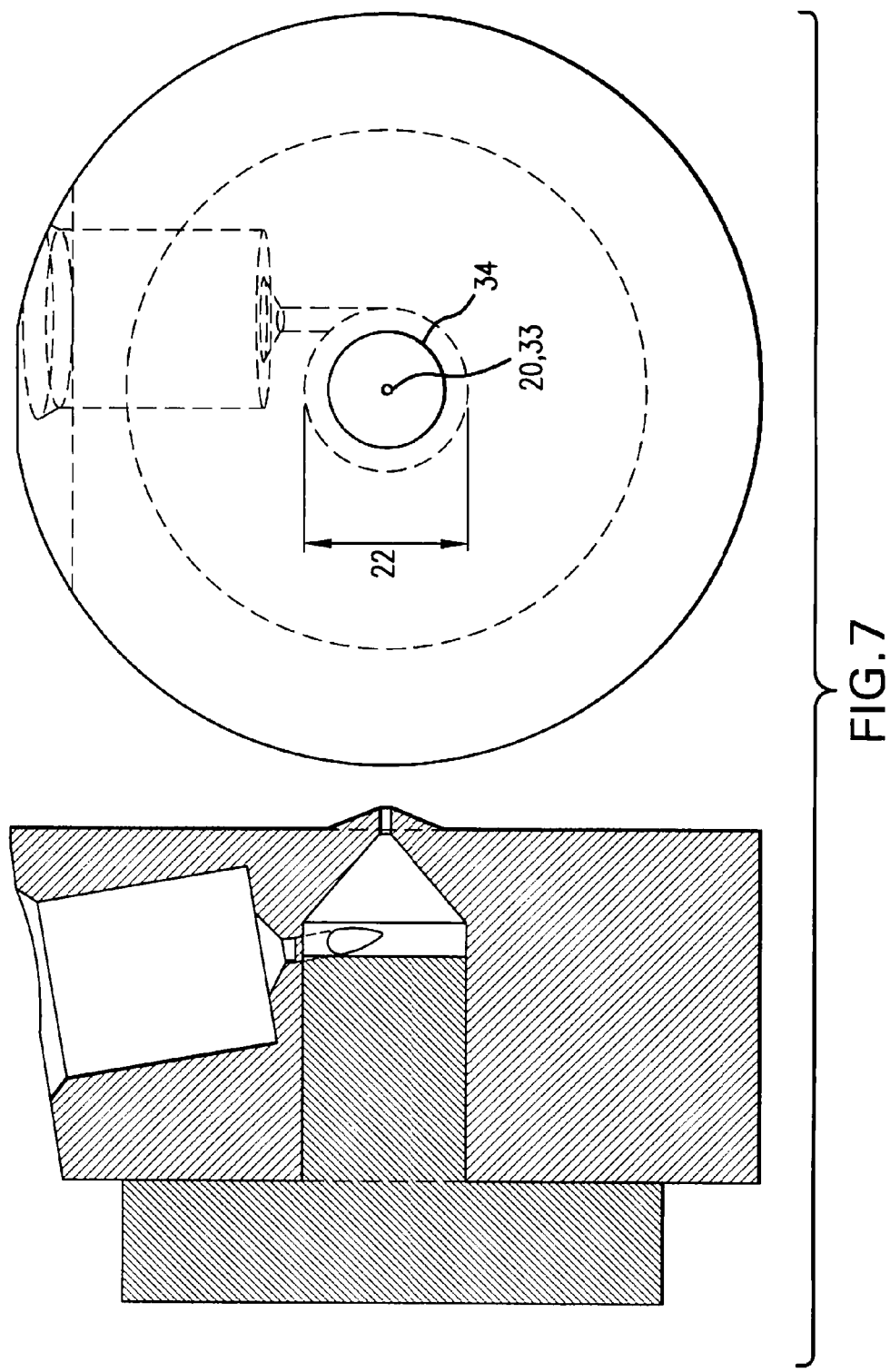
FIG. 7 is a front view of the nozzle face of the present invention showing the dimensions of a protruding nozzle face that is any configuration except trapezoidal.
Figure 8:
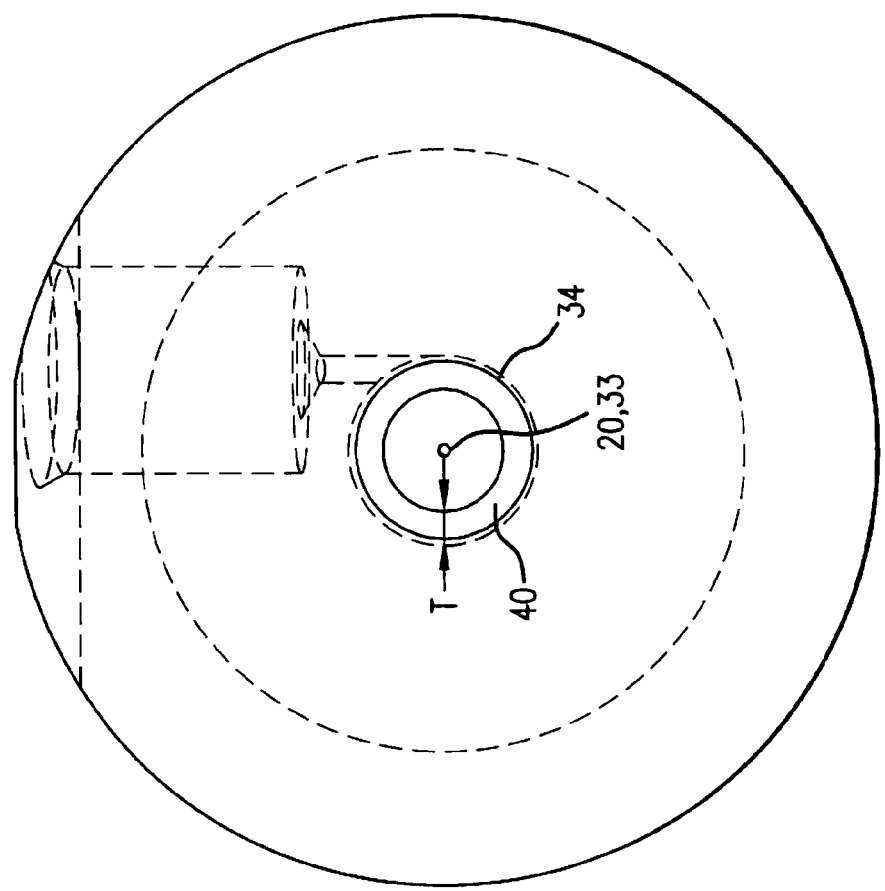
FIG. 8 is a front view of the nozzle face of the present invention showing the dimensions of a protruding nozzle face that is trapezoidal.
Figure 8:
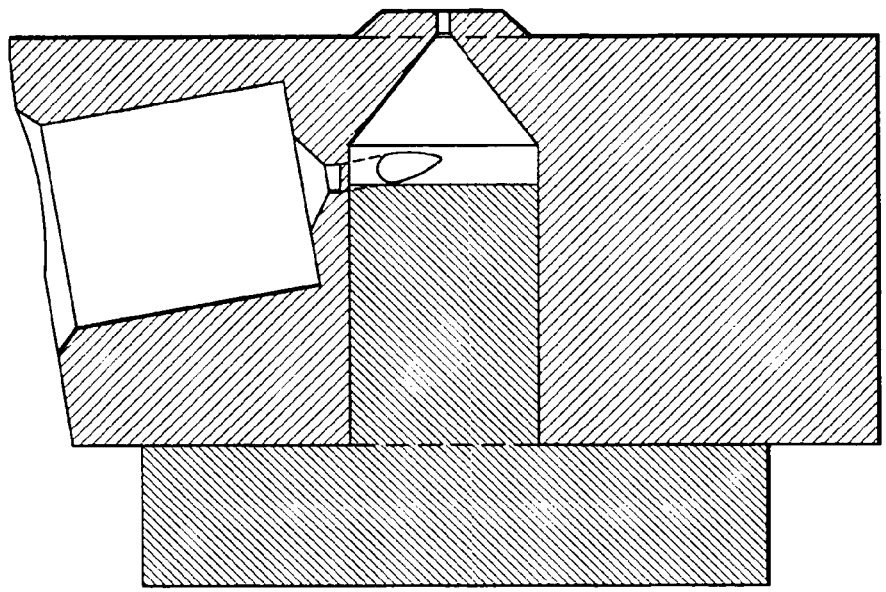

FIGS. 7 and 8 illustrate the size of the protruding ring that forms inner nozzle face 32 as compared to the relative size of the swirl chamber 12. FIG. 7 is a front view of the nozzle face of the present invention showing the protruding ring (any configuration described above except trapezoidal). Outer circumference 34 is less than the diameter of the first swirl chamber end 22 (shown in dotted lines). FIG. 8 provides a front view of the nozzle face with a trapezoidal configuration.

Figure 9:
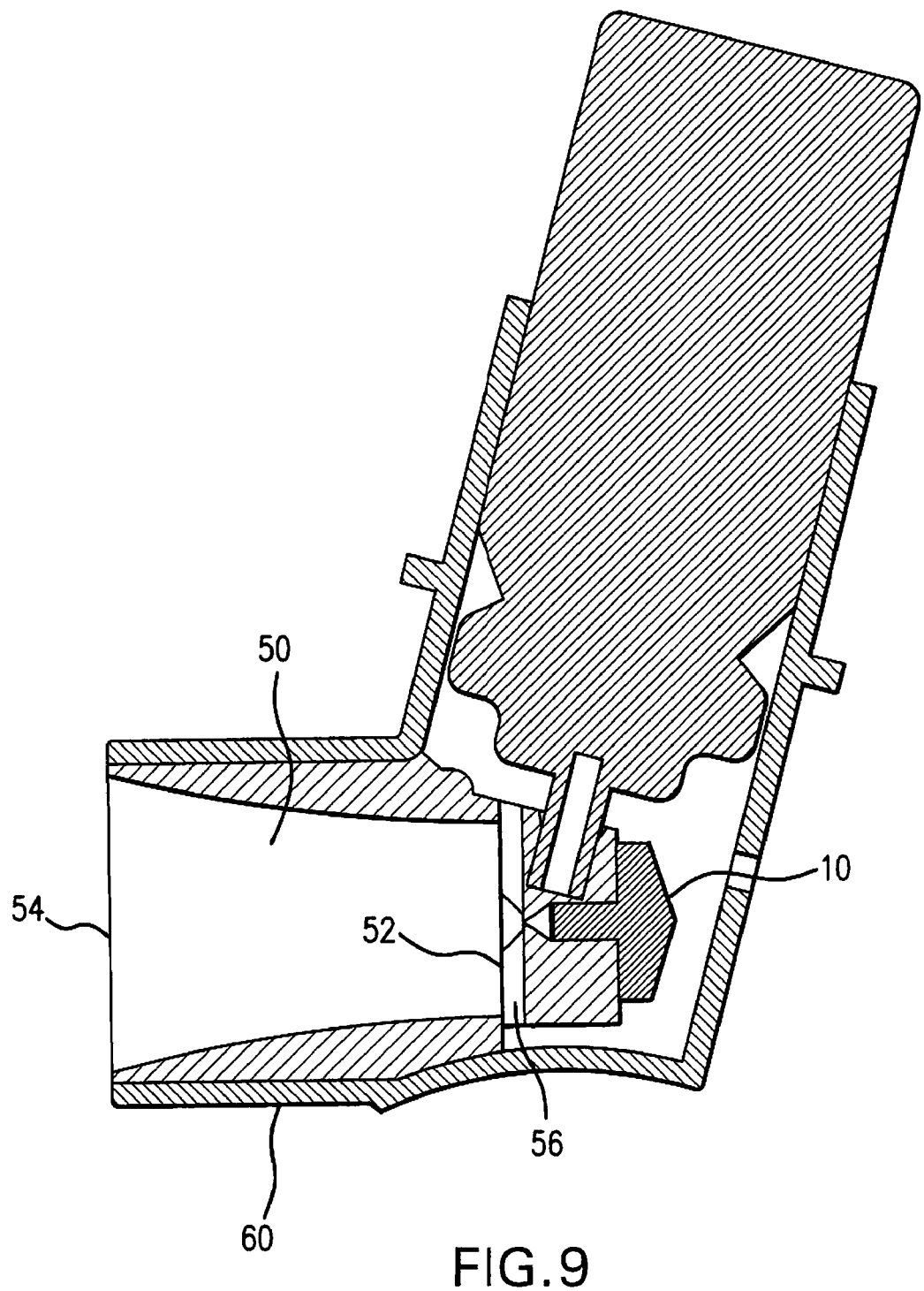
FIG. 9 is a cross sectional view of the nozzle and diverging mouthpiece insert in a standard metered dose inhaler.
Figure 10:
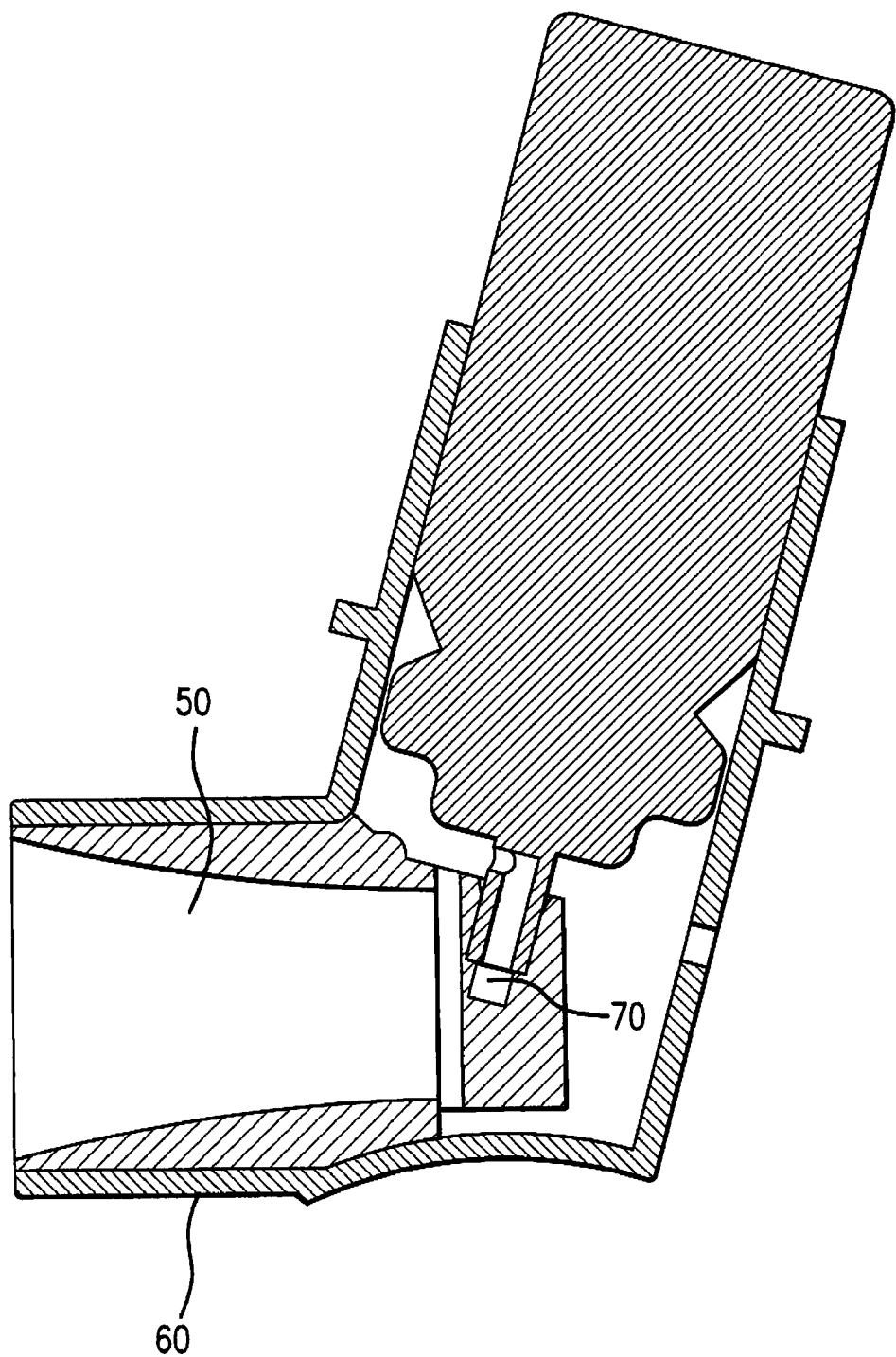
FIG. 10 is a cross sectional view of the diverging mouthpiece insert assembled with a standard sump-type MDI actuator.

FIG. 9 illustrates the diverging mouthpiece insert 50 of the present invention used in conjunction with nozzle 10 in accordance with a preferred embodiment of the present invention. For comparison purposes, FIG. 10 shows the diverging mouthpiece insert 50 with a standard sump type nozzle 70 in a metered dose inhaler, which indicates that the diverging mouthpiece insert of the present invention can be used with any type of nozzle in any type of inhaler or aerosol delivery device.

Returning to FIG. 9, insert 50 sits inside mouthpiece 60. Mouthpiece 60 can be any commercially available standard inhaler mouthpiece, either separate from (and connectable to) or manufactured as a part of the body of an inhaler. The insert 50 is operably connected to the nozzle 10 by any method contemplated by one skilled in the art. Preferably, the insert 50 is connected to the nozzle 10 by some method that permits separation of the insert from the nozzle for cleaning and other purposes. Alternatively, the insert 50 can be machined together with nozzle 10 or the mouthpiece itself. The insert 50 is not limited to connection with the nozzle 10 of the present invention, and can be used with any other nozzle configuration for aerosolized sprays.

According to one aspect of the present invention, the shape of the insert 50 is preferably round at an end 52 proximal to the nozzle 10 and gradually expands into an elliptical shape at an end 54 distal to the nozzle 10. Preferably, the cross-sectional area at the distal end 54 is more than three (3) times the cross-sectional area at the proximal end 52. For pharmaceutical/inhaler applications, the optimal insert 50 length is about one inch. Make-up air enters the insert 50 at the proximal end 52 via one or more air inlets 56 and is expelled from the device with the aerosol at the distal end 54. The increase in cross-sectional area causes a corresponding decrease in the aerosol plume velocity. The law of conservation of mass provides that the decrease in aerosol velocity is nearly inversely proportional to the increase in cross sectional area along the length of the diverging mouthpiece insert 50. According to a preferred embodiment, the diverging mouthpiece insert 50 is elliptical or oval in shape, with a minor inner diameter at the distal end 54 of approximately 0.8" a major inner diameter at the distal end 54 of approximately 1.0" and an inner diameter at the inlet of the proximal end 52 of the insert 50 of approximately 0.5".

Figure 11:
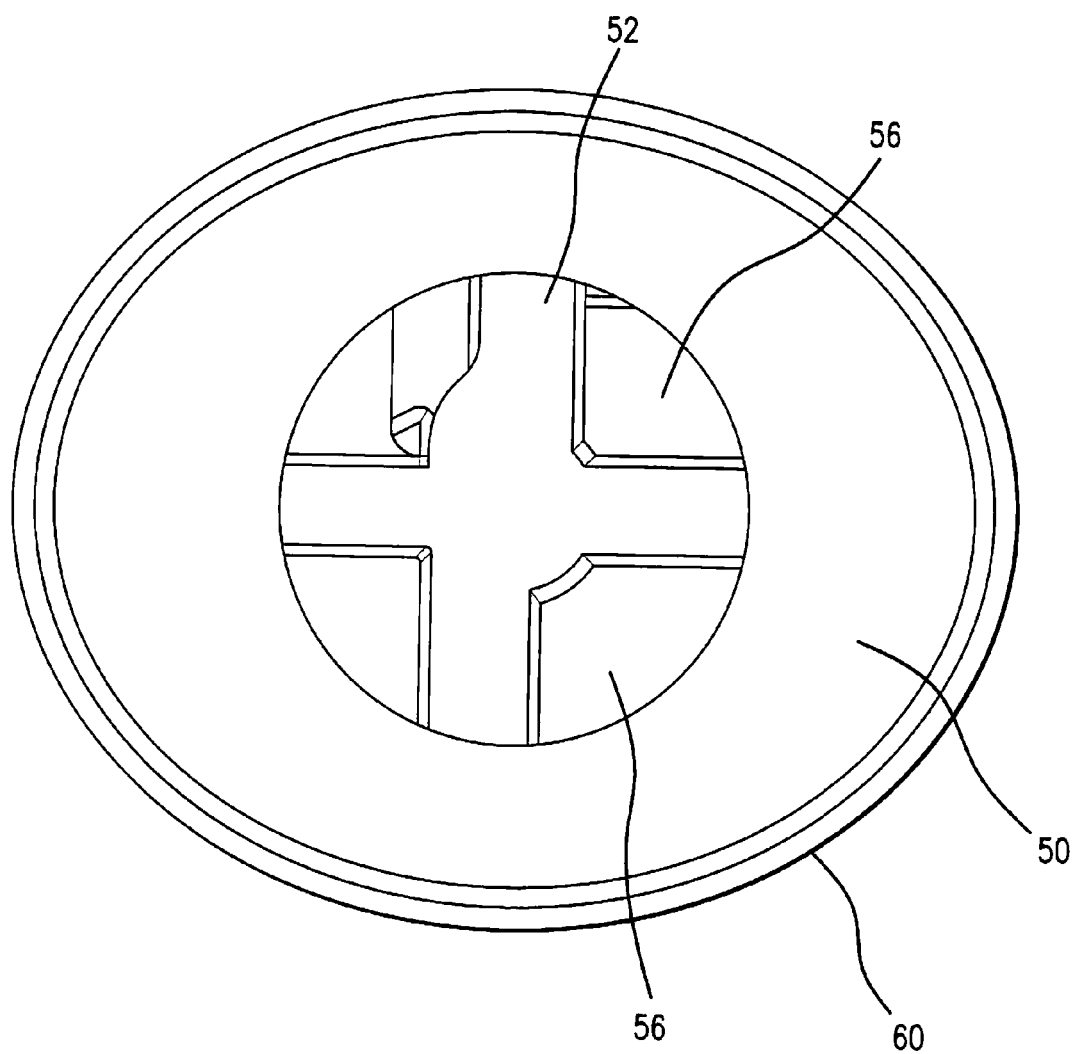
FIG. 11 is a front cross sectional view of one embodiment of the diverging mouthpiece insert.

FIG. 11 provides a different view of the diverging mouthpiece insert 50 from the front, through which an asymmetrical geometry of the air inlets 56 can be seen. Any geometry can be used at the proximal end 52 of the insert 50 to provide air inlets 56 for the aerosol make-up air. Although asymmetrical geometry can be used, the geometry of the one or more air inlets 56 is preferably symmetrical to avoid deviating the aerosol spray to one side of the insert 50 which can decrease the efficiency of spray delivery and can cause significant deposition on the walls of the insert 50.

The unexpected improvements of the atomization system of the present invention are still further achieved by the design of the flat or protruding nozzle face along with careful relative dimensioning of other nozzle components as follows. Referring to FIG. 1, the ratio of the reducing chamber inlet 26 to reducing chamber exit 18 can be from 1:1 to 3:1, preferably 2:1: the ratio of the inlet 14 diameter to the first swirl chamber end 22 diameter can be 2:1 to 10:1, preferably >5:1, the ratio of the first swirl chamber end 22 diameter to the second swirl chamber end 24 diameter can be 5:1 to 20:1, preferably 10:1: and the ratio of the exit orifice 20 diameter to length can be 0.25:1 to 4:1, preferably 1:1.

The present invention will now be described in terms of its effect on pressurized liquid that enters the nozzle 10. As shown on FIG. 1, the inlet 14 receives the pressurized liquid. Preferably, the pressurized liquid is delivered to the nozzle 10 via a valve stem (not shown) that sits inside the inlet 14. The valve stem (not shown) sits squarely on a valve stem seat 27, which is a flat, circular seat that contacts the valve stem, and surrounds the reducing chamber inlet 26. Preferably, the valve stem seat 27 fully contacts the valve stem such that there is no space or gap left at the point of contact that would otherwise allow build up or pooling of liquid on and around the tip of the valve stem at the reducing chamber inlet 26. The pressurized liquid released via the valve stem (not shown) passes through the reducing chamber inlet 26 and into the reducing chamber 16 which leads to the swirl chamber 12. Reducing chamber exit 18 imparts a high angular velocity to the liquid, creating a low-pressure central region, which creates an air-cored vortex. Generally, this vortex spins through swirl chamber 12 and emerges with tangential and axial components via exit orifice 20. The air-cored vortex is estimated to be about 80% of the orifice diameter during the main (quasi-steady) state phase of a spray event through the nozzle. The air core in conjunction with the vortex creates tremendous shear forces at the exit orifice 20 causing the exiting annular spray to break up into ligaments and droplets. This main phase of the spray event can last up to half the duration of entire spray event and results in a luminous, wide spray, which contains the bulk of the fine particles. The velocities of emerging spray droplets is typically less than the velocities at entry into the swirl chamber 12 due to dissipation of some kinetic energy during vortexing motion. As a result of the low velocity and low inertial force of the spray exiting the nozzle, and finer particle size distribution, a greater number of respirable particles reach the lung as opposed to being deposited in the device mouthpiece or throat of the patient. Towards the end of a spray event, as the metering chamber of the inhalation device empties, the propellant flow into the vortex chamber of the nozzle reduces. As a result, the diameter of the spray vapor core increases while the spray plume narrows. The spray consists largely of fine droplets emerging in pulses. Larger droplets are observed at the spray edges and occasional very large droplets are emitted in short bursts with "concave-conical" (the industry standard) nozzles.

The geometry of the flat or protruding nozzle face of the present invention prevents unvaporized drug/propellant mixture from pooling on the nozzle face because the mixture is not "shielded" by the design of the nozzle face as occurs with a standard "concave-conical" nozzle face. Any unvaporized mixture tends to be stripped frequently from the surface of the nozzle face and carried with the aerosol plume, avoiding the formation of very large droplets. As a result, the particle size distribution of the aerosol plume leaving the nozzle orifice of the present invention is finer, which also aids in more accurate deliverer of drug to the patient's lungs.

The standard conical nozzle face causes significant drug deposition on the nozzle face, as opposed to a flat nozzle face, which significantly reduces the drug deposition on the face of the nozzle. Therefore, using a flat or protruding nozzle face significantly increases the amount of drug that reaches the desired therapeutic target, e.g. the patient's lungs, in the case of a systemic drug. The reduction in drug residue around exit orifice also represents a lesser risk of orifice clogging with suspension formulations, and hence modest cleaning requirements.

Another study comparing the velocities and particle size distribution of the sprays emitted from three different actuation systems: (a) a standard actuator including a concave-conical nozzle face and standard mouthpiece (Inlet ID=0.44": outlet minor ID=0.63", major ID=0.92", optimal length=1.0"), (b) the actuator system of the present invention including a flat nozzle face and diverging mouthpiece insert (Inlet ID=0.50"; outlet minor ID=0.8", major ID=1.0", optimal length=1.0"), and (c) the commercial Proventil® actuator (mouthpiece is a tapering smooth-rectangular tube: outlet minor ID=0.58", major ID=0.77", length from nozzle=1.35"), which was chosen because of its low plume force. The aerosol velocity and droplet size were measured using phase-Doppler anemometry. A two-component LDA/PDA system from Dantec Dynamics A/S was used. Axial/horizontal and radial/vertical components of velocity as well as droplet size were measured along the mouthpiece exit plane for the three configurations. For configurations (a) and (b), the measurements were taken 30 mm from the exit orifice. The distance between the actuator orifice and the measurement plane was about 25% greater for the Proventil® configuration (c) due to the longer mouthpiece.

The velocities of the spray for the improved system were lower and limited to a smaller central area of the plume (max velocity 12.1 m/s over approximately 5 $mm^2$), compared to the velocities of the Proventil plume which are greater over a broader plume area in spite of its longer mouthpiece (max velocity 13.5 m/s over approximately 17.5 $mm^2$). The average droplet particle size of the improved system measured approximately 1.29 μm at the center of the plume, compared to approximately 2.10 μm at the center of the plume for the standard nozzle/mouthpiece configuration and approximately 1.73 μm at the center of the Proventil plume. This indicates that a greater amount of the propellant/medicament mixture is aerosolized into smaller particles exiting the device of the present invention.

As discussed above, the nozzle in accordance with the present invention is preferably connected to a diverging mouthpiece insert that also helps decelerate plume velocity. Applicants have also discovered that a larger mouthpiece on an inhalation device causes the user to open their mouth wider, increasing the tongue-to-hard-palate opening in the user's oral cavity. This promotes deep lung deposition by enabling more aerosol spray to reach the deep lung, unimpeded.

In one study the diverging mouthpiece insert (Inlet ID=0.50"; outlet minor ID=0.8", major ID=1.0", optimal length=1.0°) slowed the plume force measured at different distances ranging from 4 to 12 cm: from 28-20 mN range (using standard mouthpiece, Inlet ID=0.44": outlet minor ID=0.63", major ID=0.92", optimal length=1.0") to about 15-8 mN range (using the atomizing nozzle of the present invention with a flat-faced configuration). Plume velocity using the optimized nozzle of the present invention decreased from about 20 m/s at the start of the mouthpiece insert to less than 12 m/s at the exit plane.

In vitro testing of the mouthpiece insert of the present invention, described below, has shown that a larger mouthpiece results in decreased drug deposition inside the mouthpiece as well.

The following data is the result of in vitro testing using a suspension drug formulation for three different variations of the diverging mouthpiece insert, each using a standard "concave-conical" nozzle face to isolate the difference in results based on different geometrical configurations of the insert alone. The difference in the number of data points used for the first and second configurations is the result of faulty equipment used to measure the deposition; in the case of the third configuration, however, a "round" insert was used for comparison purposes only. Preferably, the present invention contemplates an elliptical diverging mouthpiece insert for ergonomic purposes.

TABLE 1

| Diverging Mouthpiece Insert | Horn Deposition (%) | | VNA Deposition (%) | |
|---|---|---|---|---|
| Features | Average | Std. Dev. | Average | Std. Dev. |
| Inlet ID = 0.44"; Outlet Minor ID = 0.8". Major ID = 1.0" | 7.2 | 2.3 | 4.7 | 1.2 |
| Inlet ID = 0.50"; Outlet Minor ID = 0.8". major ID = 1.0" | 5.4 | 1.5 | 4.3 | 0.7 |
| Inlet ID = 0.50"; Outlet Minor ID = major ID = 1.0" | 4.6 | 1.6 | 3.7 | 0.6 |

The data in Table 1 shows that drug deposition in the horn and nozzle decreases as the inlet and outlet diameters of the mouthpiece insert increase.

Another study was performed to illustrate the effects of the flat or protruding nozzle face in combination with the diverging mouthpiece insert, as compared to the standard convex conical nozzle face and smaller mouthpiece. Applicant used an Andersen Cascade Impactor to measure the fine particle fraction captured, simulating fine particle distribution to the lung of a patient.

TABLE 2

| Stage of Testing | Particle Size Range | Config. A (mean % age*) | Config. B (mean % age*) | Config. C (mean % age*) | Config. D (mean % age*) |
|---|---|---|---|---|---|
| VNA nozzle | N/a | 0.8 | 1.1 | 2.9 | 0.9 |
| Horn | N/a | 4.0 | 2.7 | 6.4 | 5.3 |
| Throat | >10 | 7.2 | 7.6 | 13.4 | 9.3 |
| Fine Particle Fraction (Σ of Plates 4-7. Filter) | <3.3 | 34.9 | 42.5 | 33.1 | 44.0 |
| Fine Particle Fraction (Σ of Plates 3-7. Filter) | <4.7 | 71.7 | 77.7 | 63.3 | 69.2 |
| Respirable Fraction (Σ of Plates 2-6) | 0.7-5.8 | 80.7 | 84.2 | 71.0 | 76.0 |

*mean percentage or particles deposited. based on three runs

Configuration A used a flat inner nozzle face with an elliptical mouthpiece horn of the following dimensions: 0.44" internal diameter of the mouthpiece horn inlet, a 0.8" minor axis of the mouthpiece horn outlet, and a 1.0" major axis internal diameter of the mouthpiece horn outlet.

Configuration B used a flat inner nozzle face with the preferred dimensions of the diverging mouthpiece insert: 0.5" internal diameter of the mouthpiece horn inlet, a 0.8" minor axis of the mouthpiece horn outlet, and a 1.0" major axis internal diameter of the mouthpiece horn outlet.

Configuration C used a standard concave-conical nozzle face with an elliptical mouthpiece horn of the following dimensions: 0.44" internal diameter of the mouthpiece horn inlet, a 0.63" minor axis of the mouthpiece horn outlet, and a 0.92" major axis internal diameter of the mouthpiece horn outlet.

Configuration D used a protruding convex-conical face (see FIG. 3) and the preferred diverging mouthpiece insert (0.5" internal diameter of the mouthpiece horn inlet, a 0.8" minor axis of the mouthpiece horn outlet, and a 1.0" major axis internal diameter of the mouthpiece horn outlet).

The Table 2 data shows the mean percentage of particles per spray of 35 U/actuation of rh-insulin that were captured. Deposition of large particles in the nozzle, horn, and patient throat (simulated using the uppermost plates, 0, 1 and 2, of the cascade impactor) is decreased in configurations A, B and D, which utilize the flat and protruding inner nozzle faces and elliptical mouthpiece inserts, compared to the standard inner nozzle face and smaller mouthpiece insert (configuration C). Further, the fine particle fraction captured at lower plates using cascade impact testing is greater using the flat and protruding inner nozzle faces and mouthpiece inserts (configurations A, B and D) than that using the standard inner nozzle face and standard mouthpiece (configuration C). This data illustrates that a greater amount of the drug administered to a patient in each puff or spray using one of the optimized configurations A, B or D, reaches the deep lung.

Yet another study compared drug deposition and fine particle fraction captured from the actuation system of the present invention, hereinafter termed the "VNA", to another commercialized actuator, using an Andersen Cascade Impactor. The following systems were compared:

(1) VNA of the present invention (0.010"/0.254 mm nozzle orifice, protruding convex-conical nozzle face, and mouthpiece insert-Inlet ID=0.50": outlet minor ID=0.8", major ID=1.0", optimal length=1.0"): and
(2) Valois actuator (0.012" or 0.3 mm nozzle orifice, sump nozzle, using their standard mouthpiece: straight elliptical tube, with dimensions of: outlet minor ID=0.70", outlet major ID=0.867", length from nozzle=0.75").

The results of tests on these two systems using 60 U/actuation insulin and 20 U/actuation insulin were observed. Three "sprays" or samples were taken from each canister, at both the "start" of canister life, after three priming sprays, and at the "end" of canister life, after 114 sprays total (three priming sprays, three sample sprays, and 108 "wasting" sprays).

Canisters 221, 222, and 223 contained a "rapid release" rh-insulin and HFA 134a formulation and were used for testing the Kos VNA. Table 3 provides the results of testing Cans 221, 222, and 223 containing 60 U/actuation tested in the Kos VNA at the beginning of canister life, after three priming sprays. Three samples were taken from each canister and averaged.

TABLE 3

| | | Kos VNA - 60 U/actuation, Beginning of Canister Life | | | | | | | |
|---|---|---|---|---|---|---|---|---|---|
| | Size Range | Can 221 | | Can 222 | | Can 223 | | Reported Avg. | Reported Avg. |
| Stage | (μ) | μ/Act | U/Act | μ/Act | U/Act | μ/Act | U/Act | (μ/Act) | U/Act |
| Stages | N/A | 37.572 | 0.95 | 46.12 | 1.23 | 140.847 | 3.75 | 88.26 | 1.97 |
| Neck | >10.0 | 321.425 | 8.55 | 510.34 | 13.57 | 533.227 | 141.8 | 371.85 | 12.10 |

TABLE 3-continued

Kos VNA - 60 U/actuation, Beginning of Canister Life

| Stage | Size Range (μ) | Can 221 μ/Act | Can 221 U/Act | Can 222 μ/Act | Can 222 U/Act | Can 223 μ/Act | Can 223 U/Act | Reported Avg. (μ/Act) | Reported Avg. U/Act) |
|---|---|---|---|---|---|---|---|---|---|
| Device | >10.0 | 120.563 | 3.21 | 128.36 | 3.41 | 215.923 | 5.74 | 157.26 | 4.12 |
| Plate 0 | >9.0 | 142.782 | 3.80 | 149.88 | 3.99 | 182.903 | 4.87 | 278.35 | 4.22 |
| Plate 1 | 5.8-9.0 | 265.432 | 7.06 | 235.10 | 6.25 | 283.791 | 7.55 | 283.27 | 6.95 |
| Plate 2 | 4.7-5.8 | 223.558 | 5.95 | 190.91 | 5.08 | 222.864 | 5.93 | 205.39 | 5.65 |
| Plate 3 | 3.3-4.7 | 521.997 | 13.89 | 449.44 | 11.05 | 542.386 | 14.43 | 336.88 | 13.42 |
| Plate 4 | 2.1-3.3 | 344.804 | 9.17 | 349.52 | 9.30 | 349.275 | 9.29 | 233.61 | 9.25 |
| Plate 5 | 1.1-2.1 | 167.175 | 4.45 | 191.21 | 5.09 | 201.714 | 5.37 | 119.55 | 4.97 |
| Plate 6 | 0.7-1.1 | 33.677 | 0.90 | 36.45 | 0.97 | 39.217 | 1.04 | 434.02 | 0.97 |
| Plate 7 | 0.4-0.7 | 5.747 | 0.15 | 7.51 | 0.20 | 6.518 | 0.17 | 188.08 | 0.18 |
| Filter | 0.0-0.4 | 2.655 | 0.07 | 2.93 | 0.08 | 0.264 | 0.01 | 1.95 | 0.05 |
| Total Mass Recovery* (Total emitted from Device) | N/A | 2065.00 | 54.93 | 2169.39 | 57.71 | 1606.07 | 42.72 | 1946.82 | 51.79 |
| Total Recovery (Total delivered through valve) | N/A | 2185.57 | 58.14 | 2297.76 | 61.12 | 2718.93 | 72.32 | 2400.75 | 63.86 |
| FPD** <3.3 μm | N/A | 1076.06 | 28.62 | 1037.06 | 27.59 | 1139.37 | 30.31 | 1314.10 | 28.84 |
| FPD** <4.7 μm | N/A | 1299.61 | 34.57 | 1227.97 | 32.66 | 1362.24 | 36.24 | 1519.50 | 34.49 |

*Total particulate recovery at all locations except the device
FPD = Fine Particle Dose Canisters 224, 225, and 226 contained the same rh-insulin and HFA 134***a* formulation as tested in Canisters 221 through 223 and were used for testing the Valois device. Table 4 provides the results of testing Cans 224, 225, and 226 containing 60 U/actuation in the Valois device at the beginning of canister life, after three priming sprays. Three samples were taken from each canister and averaged.

TABLE 4

Valois Device - 60 U/actuation, Beginning of Canister Life

| Stage | Size Range (μ) | Can 221 μ/Act | Can 221 U/Act | Can 222 μ/Act | Can 222 U/Act | Can 223 μ/Act | Can 223 U/Act | Reported Avg. (μ/Act) | Reported Avg. U/Act |
|---|---|---|---|---|---|---|---|---|---|
| Stages | N/A | 140.00 | 3.72 | 64.041 | 1.70 | 62.98 | 1.68 | 173.13 | 2.37 |
| Neck | >10.0 | 466.42 | 12.41 | 488.247 | 12.99 | 481.66 | 12.81 | 403.18 | 12.74 |
| Device | >10.0 | 344.27 | 9.16 | 334.889 | 8.01 | 377.34 | 10.04 | 291.96 | 9.37 |
| Plate 0 | >9.0 | 307.74 | 8.19 | 421.103 | 11.20 | 315.35 | 8.39 | 356.88 | 9.26 |
| Plate 1 | 5.8-9.0 | 278.02 | 7.40 | 224.435 | 5.97 | 254.89 | 6.78 | 244.09 | 6.72 |
| Plate 2 | 4.7-5.8 | 194.36 | 5.17 | 121.483 | 3.23 | 196.74 | 5.23 | 144.15 | 4.54 |
| Plate 3 | 3.3-4.7 | 410.01 | 10.91 | 313.20 | 8.33 | 341.79 | 9.09 | 248.00 | 9.44 |
| Plate 4 | 2.1-3.3 | 254.48 | 6.77 | 194.075 | 5.16 | 229.82 | 6.11 | 151.12 | 6.01 |
| Plate 5 | 1.1-2.1 | 134.47 | 3.58 | 113.265 | 3.01 | 116.60 | 3.10 | 82.90 | 3.23 |
| Plate 6 | 0.7-1.1 | 31.81 | 0.85 | 25.166 | 0.67 | 20.81 | 0.55 | 388.58 | 0.69 |
| Plate 7 | 0.4-0.7 | 3.93 | 0.10 | 4.234 | 0.11 | 4.79 | 0.13 | 118.20 | 0.11 |
| Filter | 0.0-0.4 | 1.45 | 0.04 | 1.206 | 0.03 | 0.95 | 0.03 | 1.20 | 0.03 |
| Total Mass Recovery* (Total emitted Dose | N/A | 2222.70 | 59.12 | 1970.46 | 52.41 | 2026.37 | 53.90 | 2073.17 | 55.15 |
| Total Recovery (Delivery through valve) | N/A | 2566.96 | 68.28 | 2305.35 | 61.32 | 2403.71 | 63.94 | 2425.34 | 64.51 |
| FPD** <3.3 μm | N/A | 836.15 | 22.24 | 651.15 | 17.32 | 714.76 | 19.01 | 989.99 | 19.52 |
| FPD* <4.7 μm | N/A | 1030.51 | 27.41 | 772.63 | 20.55 | 911.50 | 24.25 | 1134.14 | 24.07 |

*Total particulate recovery at all locations except the device
**FPD = Fine Particle Dose From these 60 U/actuation tests at the beginning of canister life, 67% of the total mass recovery using the Kos VNA was fine particles <4.7 µm. Only 44% of the total mass recovery from the Valois device was fine particles <4.7 µm. Less than 7% of the Total Recovery (which includes measurement from the device) was deposited in the device itself using the Kos VNA. Over 14% was deposited in the Valois device.

Table 5 is a summary of the data collected from all six canisters, 221 through 223 using the Kos VNA, and 224 through 226 using the Valois device at the end of the canister life, after three priming sprays, three samples and 108 wasting sprays.

TABLE 5

Summary - Kos VNA vs. Valois Device - 60 U/actuation, End of canister life

| | Kos VNA | | Valois Device | |
| --- | --- | --- | --- | --- |
| Stage | Reported Avg. (µ/Act) | Reported Avg. (U/Act) | Reported Avg. (µ/Act) | Reported Avg. (U/Act) |
| Device | 151.23 | 4.02 | 370.61 | 9.86 |
| Total Mass Recovery* (Total Emitted Dose) | 2514.91 | 66.90 | 2299.54 | 61.17 |
| Total Recovery (Delivery through valve) | 2666.14 | 70.92 | 2670.15 | 71.03 |
| FPD** <3.3 µm | 1119.49 | 29.78 | 755.91 | 20.11 |
| FPD* <4.7 µm | 1346.42 | 35.81 | 949.98 | 25.27 |

*Total particulate recovery at all locations except the device
**FPD = Fine Particle Dose From these 60 U/actuation tests at the end of canister life, 54% of the total mass recovery using the Kos VNA was fine particles <4.71 µm. Only 42% of the total mass recovery from the Valois device was fine particles <4.7 µm. Less than 6% of the particulate mass was deposited in the device using the Kos VNA, as opposed to 14% deposited in the Valois device.

The second iteration of this test was completed using canisters containing 20 U/spray of the rh-insulin/HFA 134a formulation. Canisters 221, 222, and 223 were used for testing the Kos VNA. Canisters 224, 225 and 226 were used for testing the Valois device. Table 6 below provides the results of testing Canisters 221 through 226 at the beginning of canister life. Three samples were taken from each device and averaged after three priming sprays.

TABLE 6

Summary - Kos VNA vs. Valois Device - 20 U/actuation, Beginning of canister life

| | Kos VNA | | Valois Device | |
| --- | --- | --- | --- | --- |
| Stage | Reported Avg. (µ/Act) | Reported Avg. (U/Act) | Reported Avg. (µ/Act) | Reported Avg. (U/Act) |
| Device | 81.27 | 2.16 | 113.13 | 3.01 |
| Total Mass Recovery* (Total Emitted Dose) | 900.75 | 23.96 | 712.50 | 18.95 |
| Total Recovery (Delivery through valve) | 982.02 | 26.12 | 825.63 | 21.96 |

TABLE 6-continued

Summary - Kos VNA vs. Valois Device - 20 U/actuation, Beginning of canister life

| | Kos VNA | | Valois Device | |
| --- | --- | --- | --- | --- |
| Stage | Reported Avg. (µ/Act) | Reported Avg. (U/Act) | Reported Avg. (µ/Act) | Reported Avg. (U/Act) |
| FPD** <3.3 µm | 541.86 | 14.41 | 325.96 | 8.67 |
| FPD* <4.7 µm | 602.52 | 16.03 | 386.02 | 10.27 |

*Total particulate recovery at all locations except the device
**FPD = Fine Particle Dose From these 20 U/actuation tests at the beginning of canister life, 67% of the total mass recovery using the Kos VNA was fine particles 4.7 µm. Only 54% of the total mass recovery from the Valois device was fine particles <4.7 µm. Eight percent of the total recovery was measured in the Kos VNA device, compared to 14% measured in the Valois device.

Table 7 below provides the results of testing Canisters 221 through 226 containing 20 U/actuation at the end of canister life. Three samples were taken from each device after the three priming sprays and three sample sprays and 108 wasting sprays.

TABLE 7

Summary - Kos VNA vs. Valois Device - 20 U/actuation, End of canister life

| | Kos VNA | | Valois Device | |
| --- | --- | --- | --- | --- |
| Stage | Reported Avg. (µ/Act) | Reported Avg. (U/Act) | Reported Avg. (µ/Act) | Reported Avg. (U/Act) |
| Device | 99.06 | 2.63 | 197.63 | 5.26 |
| Total Mass Recovery* (Total Emitted Dose) | 955.14 | 25.14 | 695.68 | 18.51 |
| Total Recovery (Delivery through valve) | 1054.19 | 28.04 | 893.31 | 23.76 |
| FPD** <3.3 µm | 525.54 | 13.98 | 302.47 | 8.05 |
| FPD* <4.7 µm | 594.24 | 15.81 | 358.91 | 9.55 |

*Total particulate recovery at all locations except the device
**FPD = Fine Particle Dose From these 20 U/actuation tests at the beginning of canister life, 62% of the total mass recovery using the Kos VNA was fine particles <4.7 µm. Only 52% of the total mass recovery from the Valois device was fine particles <4.7 µm. Nine percent of the total recovery was measured in the Kos VNA device, compared to 22% measured in the Valois device.

These results illustrate that at both the beginning and end of canister life, the atomization system of the present invention outperforms the Valois system. There is a significantly greater amount of drug deposited in the Valois device, from 14-22% versus less than 9% in the Kos VNA at either the beginning or end of canister life. The fine particle fraction captured from the VNA is significantly greater for both <3.3 µm and <4.7 µm. This drug deposition measurement is an indirect measurement of plume velocity, and also illustrates that the velocity of the VNA plume is less than that of the Valois plume, allowing a greater number of fine particles to reach the lower cascade impaction plate filters as opposed to being captured in the upper plates of the impactor, or the device or patient's throat.

Figure 12:
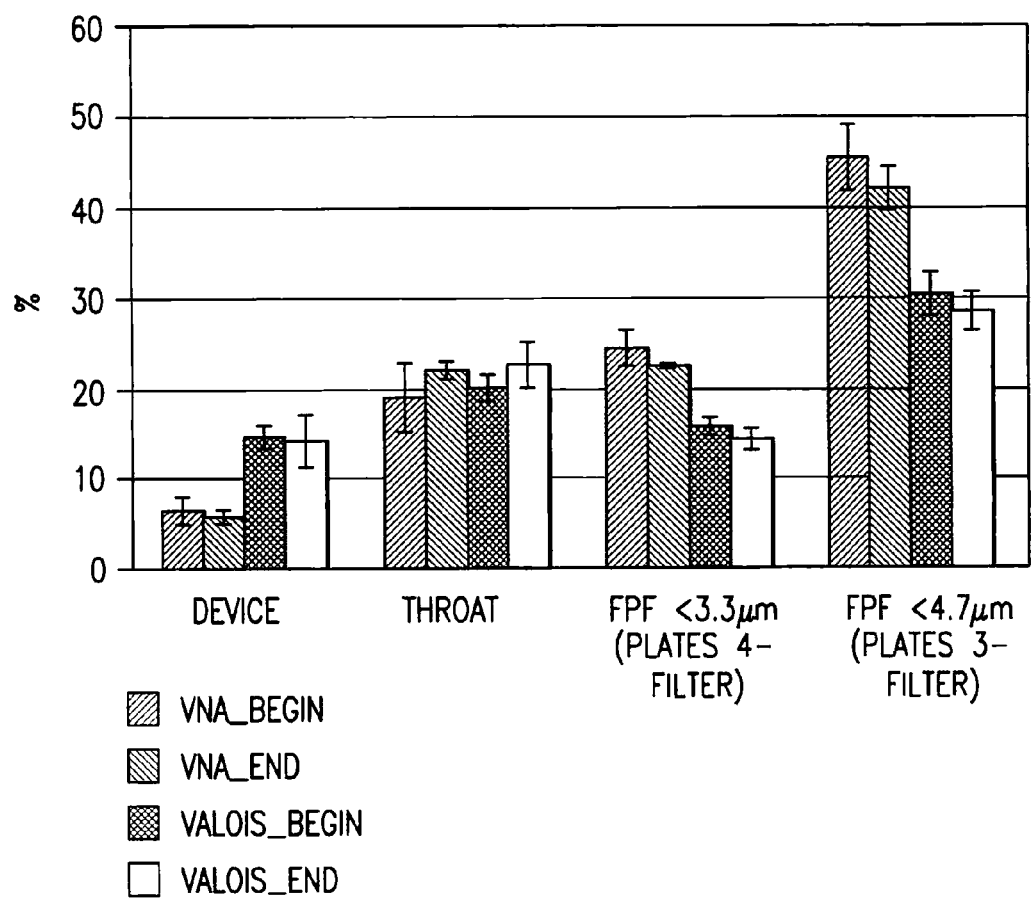
FIG. 12 is a chart illustrating the data regarding the Kos VNA versus Valois (75 µl metering valve) actuator comparison using 60 U/act Insulin Formulation, beginning of canister life.

The actuator comparison between the Kos VNA and Valois device is illustrated in FIG. 12.

The present invention can be carried out in other specific ways than those herein set forth without departing from the scope and essential characteristics of the invention. Further, the various aspects of the disclosed device and method can be used alone or in any combination, as is desired. The disclosed embodiments are. therefore, to be considered in all respects as illustrative and not restrictive, and all changes coming within the meaning and equivalency range of the appended claims are intended to be embraced therein.

What is claimed is:

1. A nozzle for producing aerosolized spray comprising:
a conical swirl chamber having a large end and a small end said large end having a diameter that is greater than the diameter of said small end:
an inlet which opens into said swirl chamber where the inlet has a longitudinal axis and enters the swirl chamber at an angle, the angle which is measured from the longitudinal axis of said swirl chamber:
a cylindrical exit orifice at, and collinear with, the small end of said swirl chamber, said exit orifice being defined by a circumference and a length and having a first end at one end of said length, which is proximal to said swirl chamber and a second end at the other end of said length which is the end distal to said swirl chamber: and
a nozzle face attached to the exterior of said exit orifice wherein said nozzle face is defined by an inner circumference, an outer circumference, and a height and wherein said inner circumference aligns with and is equal to said exit orifice circumference wherein the angle measured from said inlet longitudinal axis to said swirl chamber axis is greater than 90 degrees.

2. A nozzle for producing aerosolized spray comprising:
a conical swirl chamber having a large end and a small end said large end having a diameter that is greater than the diameter of said small end:
an inlet which opens into said swirl chamber where the inlet has a longitudinal axis and enters the swirl chamber at an angle, the angle which is measured from the longitudinal axis of said swirl chamber:
a cylindrical exit orifice at, and collinear with, the small end of said swirl chamber, said exit orifice being defined by a circumference and a length and having a first end at one end of said length, which is proximal to said swirl chamber and a second end at the other end of said length which is the end distal to said swirl chamber: and
a nozzle face attached to the exterior of said exit orifice wherein said nozzle face is defined by an inner circumference, an outer circumference, and a height and wherein said inner circumference aligns with and is equal to said exit orifice circumference wherein the angle measured from said inlet longitudinal axis to said swirl chamber axis is 105 degrees.

3. A nozzle for producing aerosolized spray comprising:
a conical swirl chamber having a large end and a small end said large end having a diameter that is greater than the diameter of said small end:
an inlet which opens into said swirl chamber where the inlet has a longitudinal axis and enters the swirl chamber at an angle, the angle which is measured from the longitudinal axis of said swirl chamber:
a cylindrical exit orifice at, and collinear with, the small end of said swirl chamber, said exit orifice being defined by a circumference and a length and having a first end at one end of said length, which is proximal to said swirl chamber and a second end at the other end of said length which is the end distal to said swirl chamber: and a nozzle face attached to the exterior of said exit orifice wherein said nozzle face is defined by an inner circumference, an outer circumference, and a height and wherein said inner circumference aligns with and is equal to said exit orifice circumference wherein said swirl chamber has a cone angle of 60 to 120 degrees.

4. A nozzle for producing aerosolized spray comprising:
a conical swirl chamber having a large end and a small end said large end having a diameter that is greater than the diameter of said small end:
an inlet which opens into said swirl chamber where the inlet has a longitudinal axis and enters the swirl chamber at an angle, the angle which is measured from the longitudinal axis of said swirl chamber:
a cylindrical exit orifice at, and collinear with, the small end of said swirl chamber, said exit orifice being defined by a circumference and a length and having a first end at one end of said length, which is proximal to said swirl chamber and a second end at the other end of said length which is the end distal to said swirl chamber: and a nozzle face attached to the exterior of said exit orifice wherein said nozzle face is defined by an inner circumference, an outer circumference, and a height and wherein said inner circumference aligns with and is equal to said exit orifice circumference further comprising a mouthpiece insert coupled to said nozzle said mouthpiece insert having a proximal end and a distal end, wherein said proximal end is located near said nozzle, and wherein said cross-sectional area of said distal end is approximately three times the cross-sectional area of said proximal end.

5. The nozzle of claim 4 wherein said insert has an internal diameter of approximately 0.4 to 0.6 inches at said proximal end, an internal diameter of approximately 0.75 to 1.25 inches as said distal end, and a length of approximately 0.75 to 1.5 inches.

6. An improved nozzle for producing low-plume aerosolized sprays wherein said nozzle includes a housing and an inlet which opens into a swirl chamber having a longitudinal axis, an outer circumference, a diameter, and a first swirl chamber end having a diameter, said inlet having a longitudinal axis and being tangential to said outer circumference and set at an angle to said first swirl chamber end, an exit passage having a circumference at each of a first exit passage end, and a second exit passage end distal to a second swirl chamber end having a diameter, said diameter of said first swirl chamber end having a diameter greater than said diameter of said second swirl chamber end, said exit passage communicating with a nozzle face through which an aerosol is discharged, the improvement comprising a nozzle face which is a raised concentric ring surrounding said exit passage where said ring is defined by an inner circumference, an outer circumference, and a height wherein said ring inner circumference aligns with and is equal to said second exit passage end circumference and wherein the angle measured from said inlet axis to said swirl chamber axis is greater than 90 degrees.

7. An improved nozzle for producing low-plume aerosolized sprays wherein said nozzle includes a housing and an inlet which opens into a swirl chamber having a longitudinal axis, an outer circumference, a diameter, and a first swirl chamber end having a diameter, said inlet having a longitudinal axis and being tangential to said outer circumference and set at an angle to said first swirl chamber end, an exit passage having a circumference at each of a first exit passage end, and a second exit passage end distal to a second swirl chamber end having a diameter, said diameter of said first swirl chamber end having a diameter greater than said diameter of said second swirl chamber end, said exit passage communicating with a nozzle face through which an aerosol is discharged, the improvement comprising a nozzle face which is a raised concentric ring surrounding said exit passage where said ring is defined by an inner circumference, an outer circumference, and a height wherein said ring inner circumference aligns with and is equal to said second exit passage end circumference and wherein the angle measured from said inlet axis to said swirl chamber axis is 105 degrees.

8. An improved nozzle for producing low-plume aerosolized sprays wherein said nozzle includes a housing and an inlet which opens into a swirl chamber having a longitudinal axis, an outer circumference, a diameter, and a first swirl chamber end having a diameter, said inlet having a longitudinal axis and being tangential to said outer circumference and set at an angle to said first swirl chamber end, an exit passage having a circumference at each of a first exit passage end, and a second exit passage end distal to a second swirl chamber end having a diameter, said diameter of said first swirl chamber end having a diameter greater than said diameter of said second swirl chamber end, said exit passage communicating with a nozzle face through which an aerosol is discharged, the improvement comprising a nozzle face which is a raised concentric ring surrounding said exit passage where said ring is defined by an inner circumference, an outer circumference, and a height wherein said ring inner circumference aligns with and is equal to said second exit passage end circumference and wherein said swirl chamber has a cone angle of 60 to 120 degrees.

9. An improved nozzle for producing low-plume aerosolized sprays wherein said nozzle includes a housing and an inlet which opens into a swirl chamber having a longitudinal axis, an outer circumference, a diameter, and a first swirl chamber end having a diameter, said inlet having a longitudinal axis and being tangential to said outer circumference and set at an angle to said first swirl chamber end, an exit passage having a circumference at each of a first exit passage end, and a second exit passage end distal to a second swirl chamber end having a diameter, said diameter of said first swirl chamber end having a diameter greater than said diameter of said second swirl chamber end, said exit passage communicating with a nozzle face through which an aerosol is discharged, the improvement comprising a nozzle face which is a raised concentric ring surrounding said exit passage where said ring is defined by an inner circumference, an outer circumference, and a height wherein said ring inner circumference aligns with and is equal to said second exit passage end circumference and further comprising a mouthpiece insert coupled to said nozzle said mouthpiece insert having a proximal end and a distal end, wherein said proximal end is attached to said nozzle, and wherein said cross-sectional area of said distal end is approximately three times said cross-sectional area of said proximal end.

10. The nozzle of claim 9 wherein said insert has an internal diameter of approximately 0.4 to 0.6 inches at said proximal end, an internal diameter of approximately 0.75 to 1.25 inches as said distal end and a length of approximately 0.75 to 1.5 inches.

\* \* \* \* \*